United States Patent [19]

Beale

[11] Patent Number: 5,549,673
[45] Date of Patent: Aug. 27, 1996

[54] PHONOSURGERY IMPLANT INSTRUMENTS AND A SYSTEM AND METHOD OF IMPLANTATION

[75] Inventor: Bradford W. Beale, Memphis, Tenn.

[73] Assignee: Smith & Nephew Richards Inc., Memphis, Tenn.

[21] Appl. No.: 118,097

[22] Filed: Sep. 8, 1993

Related U.S. Application Data

[63] Continuation of Ser. No. 511,454, Apr. 20, 1990, abandoned.

[51] Int. Cl.$^6$ .............................. A61F 2/20; A61F 2/02; A61F 2/00; A61B 19/00
[52] U.S. Cl. ................................ 623/9; 623/11; 623/66; 600/37; 606/196; 128/898
[58] Field of Search ............................ 600/32; 606/102, 606/99, 191, 196; 623/9, 11, 13–14, 66; 128/897–899

[56] References Cited

U.S. PATENT DOCUMENTS

| 3,547,115 | 12/1970 | Stevens ................................ 606/102 |
| 3,707,150 | 12/1972 | Montgomery . | |
| 3,818,894 | 6/1974 | Wichterle . | |
| 4,566,466 | 1/1986 | Ripple et al. ............................ 606/102 |
| 5,156,626 | 10/1992 | Broderick et al. ........................ 623/16 |
| 5,197,982 | 3/1993 | Goldsmith, III et al. ................... 623/9 |
| 5,201,765 | 4/1993 | Netterville et al. .......................... 623/9 |
| 5,314,470 | 5/1994 | Persson ....................................... 623/9 |
| 5,326,375 | 7/1994 | Montgomery et al. . | |

FOREIGN PATENT DOCUMENTS

| 0709074 | 1/1980 | U.S.S.R. .................................... 623/9 |

OTHER PUBLICATIONS

Glenn Isaacson, Cameron J. Krichner, Jung H. Kim and John A. Kirschner, *Histology of Isshiki in Thyroplasty Type I*, 99:42–45, 1990.

Nobuhiko Isshiki, Hisayoshi Kojima, Tatsuzo Taira and Kazuhiko Shoji, *Recent Modifications in Thyroplasty Type I*, 98:777–779, 1989.

Nobuhiko Isshiki, Masahiro Tanabe and Masaki Sawada, *Arytenoid Adduction for Unilateral Vocal Cord Paralysis*, 104:555–558, 1978.

James A. Koufman, *Laryngoplasty for Vocal Cord Medialization: An Alternative to Teflon®*, 96:726, 728, 730, 1986.

James A. Koufman, *Laryngoplastic Phonosurgery*, 339, 381, 343, 347, 349, 1988.

James A. Koufman, *Surgical Correction of Dysphonia Due to Bowing of the Vocal Cords*, 98:41, 43, 45.

Michael D. Maves, Brian F. McCabe and Steven Gray, *Phonosurgery: Indications and Pitfalls*, 98:577–580, 1989.

Hans von Leden, Jean Abitbol, Marc Bouchayer, Minoru Hirano and Harvey Tucker, *Phonosurgery*, 3:2:175–182, 1989.

Adams, Crawford, Acetabulum Gauge, date unknown.

Richards, Acetabular Gage Measuring Jet, Journal of Bone & Joint Surgery, vol. 45–A #6, Sep. 1963.

*Primary Examiner*—Mary Beth Jones
*Assistant Examiner*—Karin M. Reichle
*Attorney, Agent, or Firm*—Pravel, Hewitt, Kimball & Krieger

[57] ABSTRACT

A phonosurgery implant is inserted through an opening in the thyroid cartilage to reposition and stabilize a vocal cord. An implant body is formed of a biocompatible material. The body includes a contact surface adapted to support a vocal cord upon insertion through an opening in the thyroid cartilage, the body being shaped to move in the opening so a surgeon can position the body for optimum vocal cord operation. The body also includes a holding portion away from the contact surface, the holding portion being shaped to be engaged and held by an instrument for inserting and moving the implant body in the opening. The holding portion is engaged and held by a shim in a fixed position in the opening and relative to the vocal cord.

3 Claims, 4 Drawing Sheets

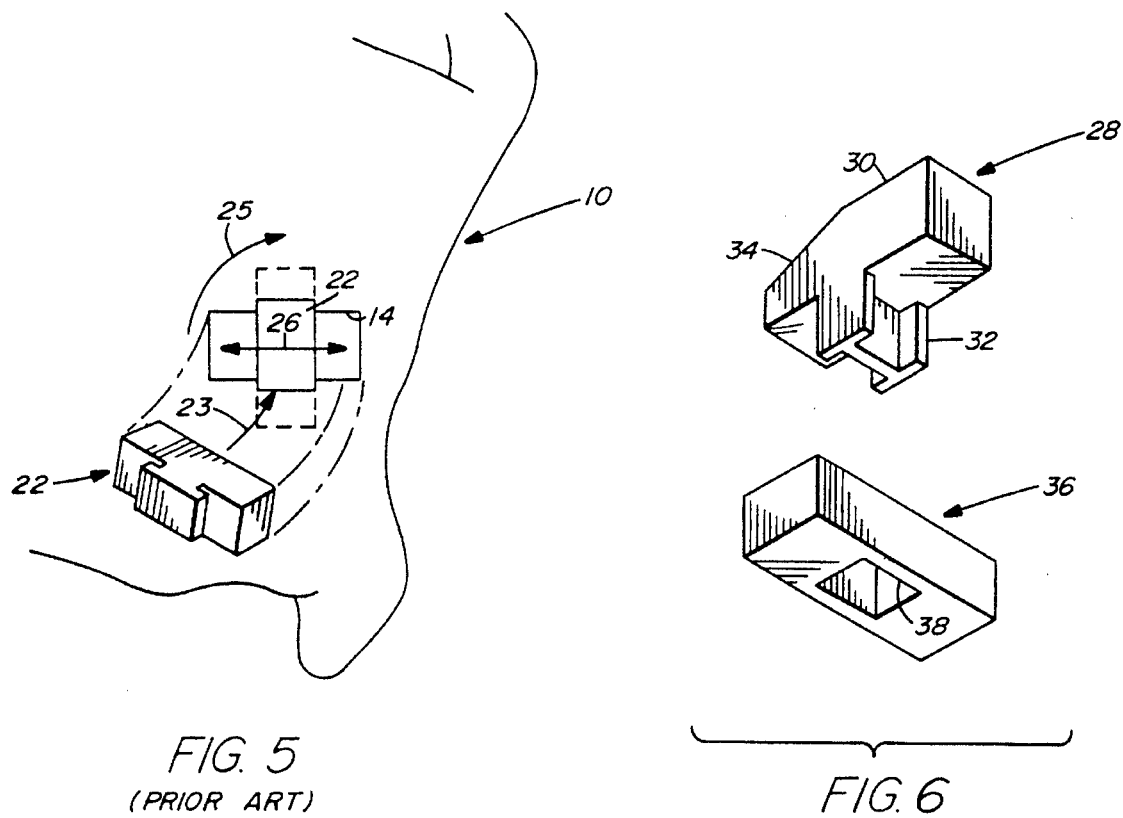
FIG. 5
(PRIOR ART)
FIG. 6
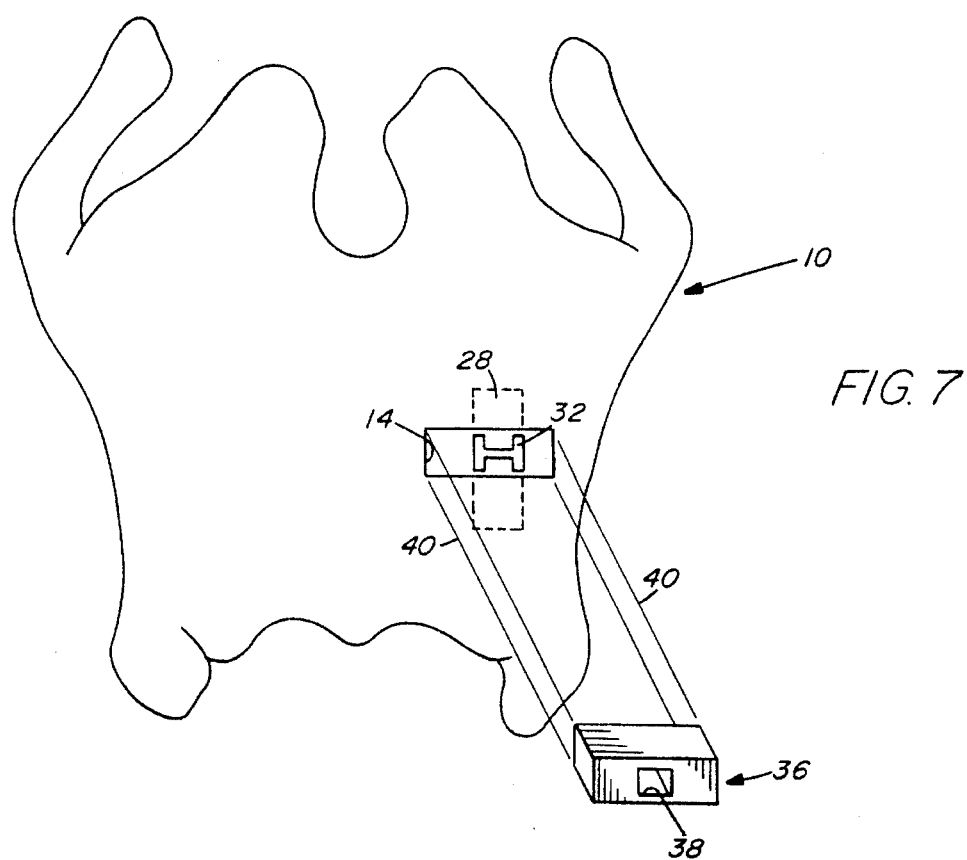
FIG. 7

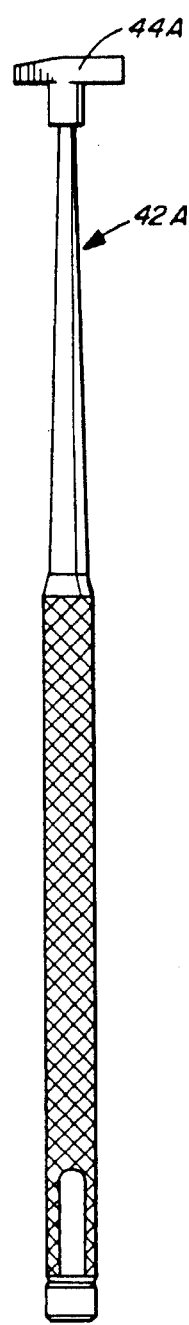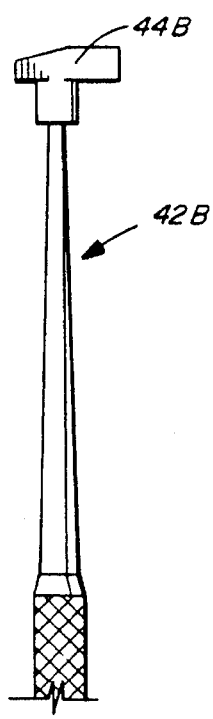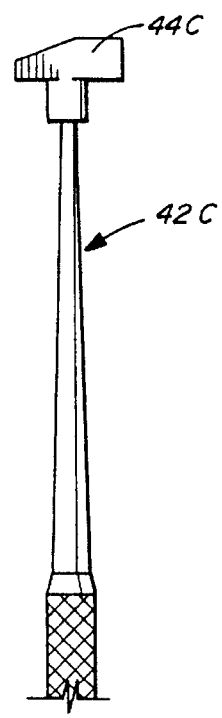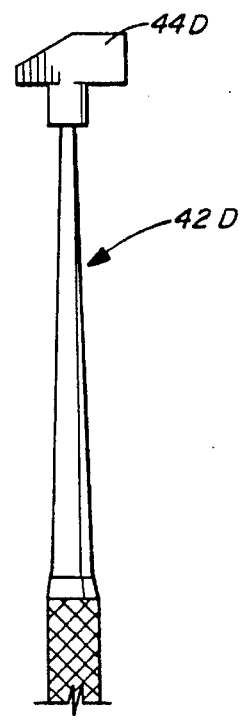
FIG. 8A    FIG. 8B    FIG. 8C    FIG. 8D
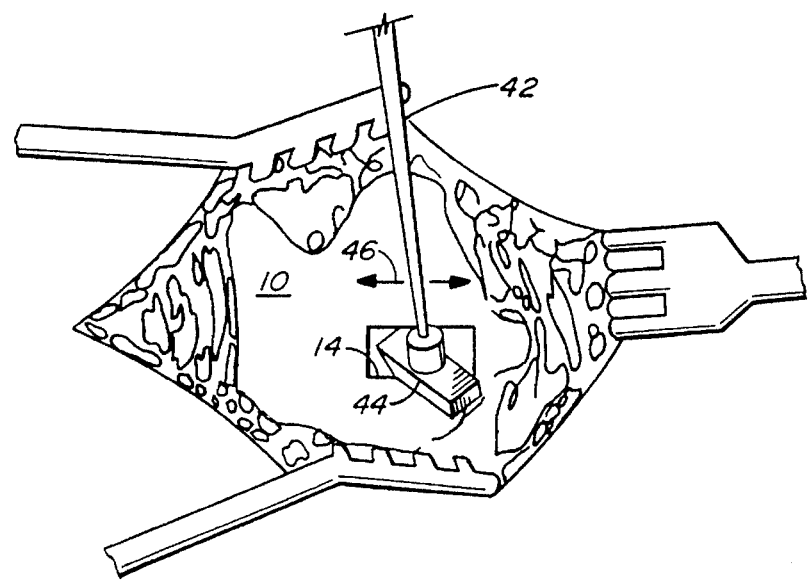
FIG. 9

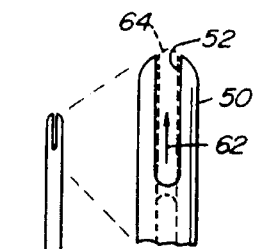
FIG. 11B
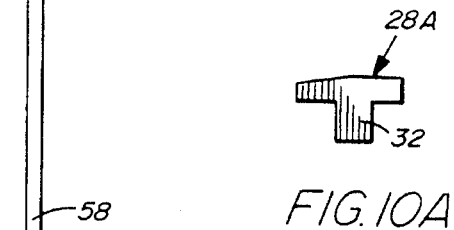
FIG. 10A   FIG. 10B   FIG. 10C   FIG. 10D
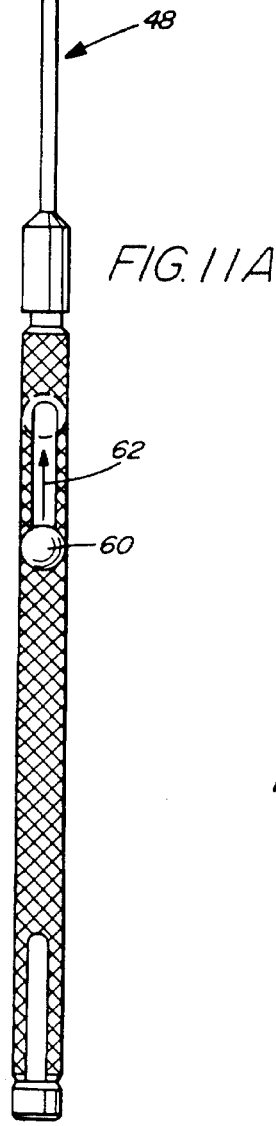
FIG. 11A
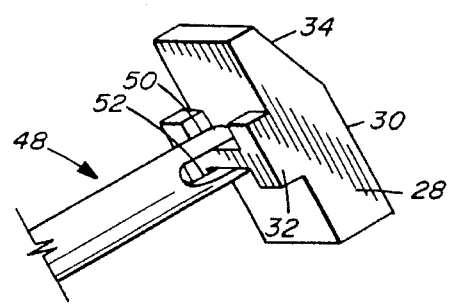
FIG. 12
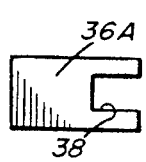 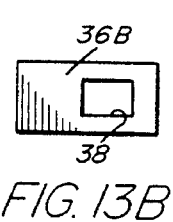 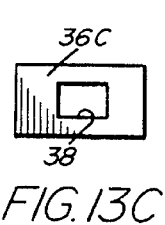
FIG. 13A   FIG. 13B   FIG. 13C   FIG. 13D
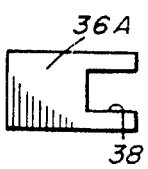 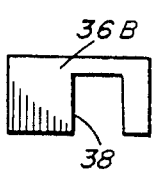 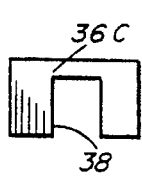 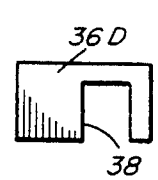
FIG. 14A   FIG. 14B   FIG. 14C   FIG. 14D

PHONOSURGERY IMPLANT INSTRUMENTS AND A SYSTEM AND METHOD OF IMPLANTATION

This is a continuation of application Ser. No. 07/511,454 filed on Apr. 20, 1990, now abandoned.

BACKGROUND OF THE INVENTION

This invention relates to the field of phonosurgery and, more particularly, to implants, instruments and a method of implantation for surgically medializing a paralyzed or bowed vocal cord.

It is well known that sound is produced in human beings through the passage of air past a pair of vocal cords located in the larynx. Muscles in the larynx operate to vary tension in the vocal cords to regulate them to produce speech and prevent aspiration of foreign particles into the lung.

When one of the vocal cords becomes paralyzed or immobile, voice quality is impaired because tension in the vocal cord cannot be regulated. A controllable tension in the vocal cord or spacing between it and the operable vocal cord cannot be maintained to provide the necessary vibratory sounds required for speech. Vocal cord paralysis can be caused by cancer, trauma or other affliction which would render the vocal cord unable to be tensioned.

It has long been recognized that a paralyzed vocal cord can be repositioned or supported to remain in a fixed location relative to the other operable vocal cord so that unilateral vibration of the other vocal cord can result in acceptable voice patterns. A surgical procedure has been performed through the years by forming an opening in the thyroid cartilage and providing various means for supporting or repositioning the paralyzed vocal cord.

One approach has been to inject "TEFLON" into the paralyzed cord to increase its bulk. This procedure is considered unacceptable because of the inability of the injected "TEFLON" to close large glottic gaps and the tendency of "TEFLON" to induce fibrous reaction. It is also difficult to remove "TEFLON" from the paralyzed vocal cords, if necessary or desirable, at a later date.

A more acceptable approach has been found for supporting the disabled cord, which involves the use of a custom-fitted block of siliconized rubber known as "SILASTIC". The proper size and shape of the block are determined by the operating physician, who hand carves it during the surgical procedure, in order to fine-tune the ability of the patient to phonate or speak. Such blocks have taken the form of wedges which are totally implanted within the thyroid cartilage (see FIG. 3) or flanged plugs that can be moved back and forth in the opening in the thyroid cartilage to fine-tune the voice of the patient (see FIGS. 4 and 5).

Although these implants have proved successful and superior over the "TEFLON" injection method, dissatisfaction has been expressed because the surgical procedure requires too much time, either through custom sizing of an implant, difficulty in inserting the implant or lack of efficient method of locking the implant in place. This is a drawback because in order for a patient's voice to be fine-tuned, the patient must be kept under local anesthesia so he or she can produce sounds to test the positioning of the implant.

While being operated upon, the patient can only phonate a limited period of time so that the longer the operation and the more times the patient's voice has to be tested, the less likely that the patient's voice can be fine tuned to its optimum level. Vocal cord edema, due to a prolonged procedure, also interferes with an optimal surgical result. Therefore, there exists a need for an implant which can quickly and simply be sized and manipulated so it can be located in the proper position relative to the paralyzed vocal cord for fine tuning a patient's voice.

SUMMARY OF THE INVENTION

A phonosurgery implant, associated instruments and a method of implantation have been developed in accordance with the invention, which solve the problems discussed above. The implant, which is designed for insertion through an opening formed in the thyroid cartilage, includes an implant body formed of a biocompatible material. The body includes a contact surface which is adapted to exert pressure on, support and medialize a vocal cord upon insertion through the opening in the thyroid cartilage. The body is shaped so that it can move back and forth in the opening so the surgeon can position the body for optimum vocal cord operation.

The body includes a holding portion or neck projecting from the contact surface, the holding portion being shaped to be engaged and held by an instrument for inserting and placing the implant in the opening. A shim or holder is provided for engaging the insert and holding it in a fixed position in the opening for optimum vocal cord operation.

Before the implant is inserted, however, a series of sizing instruments can be used which have sizing heads identical in size and shape to a corresponding number of implant bodies. After an opening is formed in the thyroid cartilage, a physician can select one of the sizing instruments, insert it through the opening to a position adjacent to the vocal cord and have the patient phonate in order to determine whether the implant is of an appropriate size.

If the patient's phonation is close to being acceptable, the sizer can be moved back and forth in the opening for determining the optimum position of the implant. If the implant is not of the right thickness, another sizing instrument with a sizing head of a different thickness can be used and the procedure repeated.

After the optimum size and position of the implant are determined, the physician can easily remove the sizing instrument and select an implant which matches the size and shape of the sizing head. An inserter instrument with a notched head engages a cooperatingly-shaped holding portion of the implant and inserts it to the proper position within the opening in the thyroid cartilage.

While the implant is held in place, a shim or holder which is adapted to fit within the opening in the thyroid cartilage and engage the holding portion of the implant is moved into place, at which time a simple pushing of the physician's thumb moves a telescoping rod within the instrument to disengage the implant from the instrument. The skin over the thyroid cartilage is then returned to its proper position and the incision is sutured, which operates to hold the shim in place within the opening formed in the thyroid cartilage.

In this way, a solid backing reinforcement is implanted in minimal time for the paralyzed vocal cord so the patient has improved voice quality and a reduction in the occurrence of aspiration.

BRIEF DESCRIPTION OF THE DRAWINGS

A better understanding of the invention can be obtained from the following detailed description of the preferred embodiments of the invention when considered in conjunction with the following drawings, in which:

FIG. 5 is a closeup view of an opening formed in the thyroid cartilage to illustrate how the implant of Fib. 4 is inserted and moved to fine tune a patient's phonation;

FIG. 6 is a perspective view of an implant, including a body portion and shim, formed in accordance with the invention;

FIG. 7 is a frontal view of a thyroid cartilage showing how the implant of FIG. 6 is located in the opening;

FIGS. 8A–D are plan views of a typical set of sizing instruments used in accordance with the invention;

FIG. 9 is a partial view of a thyroid cartilage showing how a sizing instrument is used;

FIGS. 10A–D are plan views of a series of implants which correspond to the sizing instruments of FIGS. 8A–D;

FIG. 11 is a plan view of an inserting instrument for the implants of FIGS. 10A–D, with the engaging end enlarged to show the internal telescoping rod for disengaging the implant;

FIG. 12 is a perspective view showing an inserting instrument engaging an implant;

FIGS. 13A–D are plan views of a series of shims used for the implants of FIG. 10; and FIGS. 14A–D are plan views of a series of shims similar to those in FIGS. 13A–D, but having open-ended openings.

DETAILED DESCRIPTION OF PREFERRED EMBODIMENTS

Figure 1:
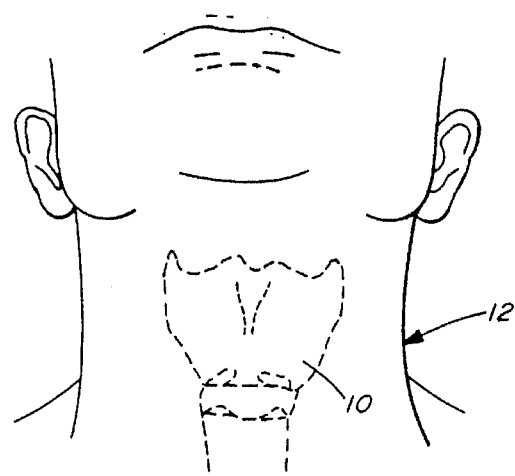
FIG. 1 is a front view of a patient's neck with the thyroid cartilage shown by the broken lines.
Figure 2:
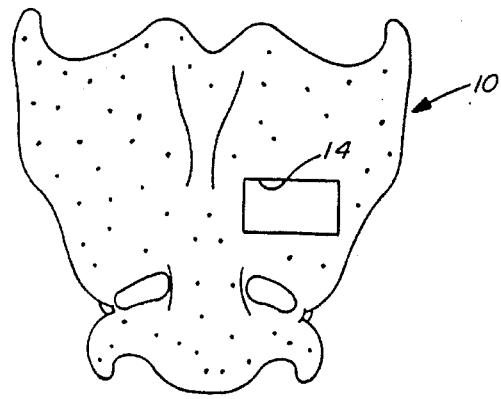
FIG. 2 is a front view of the thyroid cartilage with an opening formed in it to allow access to one of the vocal cords.

FIG. 1 shows a patient with his or her chin tilted upwardly to illustrate the location of the thyroid cartilage 10 which defines the larynx in a neck 12, where the vocal cords are located. As shown in FIG. 2, in order to gain access to one of the vocal cords of the patient, an opening 14 is formed in one side of the thyroid cartilage 10. It should be understood that an opening 14 could be formed in either side of the thyroid cartilage 10, depending on which vocal cord is paralyzed.

Figure 3:
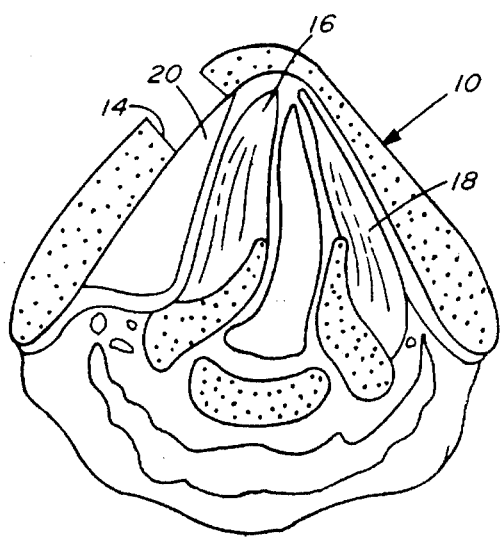
FIG. 3 is a cross-sectional view of a neck of a patient as shown in FIGS. 1 and 2, and showing a wedge of material as used in the prior art.
Figure 4:
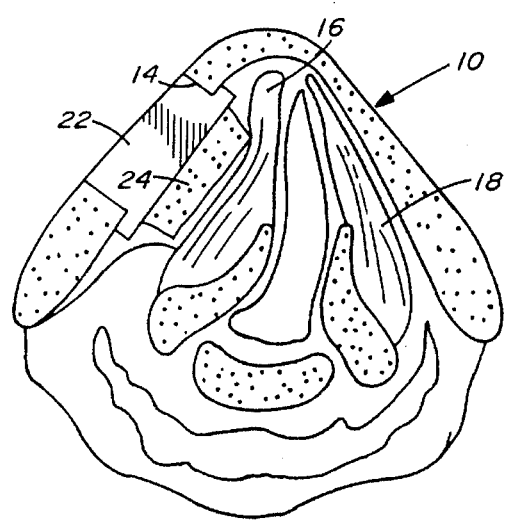
FIG. 4 is a sectional view similar to that of FIG. 3 and showing a T-shaped piece of material to hold a piece of cartilage against the vocal cord as used in the prior art.

FIGS. 3 and 4 are section views of the thyroid cartilage 10 and illustrate several types of implants which have been inserted in the prior art through an opening 14 in order to reposition a paralyzed vocal cord 16 so that it can be supported in a fixed position relative to an operational vocal cord 18 to allow the patient to phonate.

In FIG. 3, a wedge 20 formed of a silicon rubber material known as "SILASTIC" has been inserted to provide support for the vocal cord 16. The optimum size of the insert 20 is determined through trial and error with the physician removing and shaping the insert as the patient phonates to determine the optimum size and shape for the implant 20.

Another type of implant 22 is shown in FIG. 4 where a wedge of the same "SILASTIC" material is used to hold a piece of cartilage 24 against the paralyzed vocal cord 16 for the needed support. As shown best in FIG. 5, the wedge 22 is generally T-shaped and has a length and width generally similar to but smaller than that of the opening 14 to allow the implant to be inserted, as shown by arrow 23, and rotated to the position in FIG. 5, as shown by arrow 25, where it can be moved back and forth in the direction of arrow 26 to determine the optimum position. This is done after a satisfactory size is determined by inserting and resizing the implant. The implant is then sutured in place.

The present invention is an improvement over the implants and procedures shown in FIGS. 3–5. In accordance with the invention, an implant is provided as shown in FIG. 6 which includes a body portion 28 that is shaped and dimensioned to fit through a typical opening 14 formed in the thyroid cartilage and provide support for a paralyzed vocal cord.

The body 28 is generally a rectangular solid formed with a surface 30 for engaging the vocal cord and an H-shaped holding portion or neck 32 which can be held by a suitable instrument as described below. The body 28 also includes a sloped surface 34 to allow easy insertion through the opening 14. A holder or shim 36, which is sized to fit comfortably within the opening 14 for holding the body portion 28 in place, includes an opening 38 for receiving the neck 32 and holding the implant 28 at the optimum position within the opening 14 and against the paralyzed vocal cord 16.

FIG. 7 shows the implant 28 in place in opening 14 in the thyroid cartilage 10 where the body portion of the implant 28 is illustrated by broken lines to show its position behind the thyroid cartilage 10. The position of the shim 36 relative to the opening 14 is illustrated by showing the projected location through the elevational arrows 40. As discussed below, the operating physician has a series of shims 36 with openings 38 in different locations for holding the implant in various positions along the length of the opening 14.

As shown in FIGS. 10A–D, a series of implants 28A–D are provided to the physician so that the optimum implant can be used without the physician having to carve or otherwise shape one of the proper size. Determining the proper sized implant 28 is accomplished through the use of a series of sizing instruments 42A–D, shown in FIGS. 8A–D, with sizing heads 44A–D identical in size and shape to the body portions of a corresponding series of implants 28A–D as illustrated in FIGS. 10A–D.

As shown in FIG. 9, the sizer head 44 of a selected instrument 42 is easily insertable into the opening 14. The head 44 is rotated to where it is in the same position as the implant 28 as shown in FIG. 7. Afterwards, the physician has the patient phonate to determine the level of performance. If the performance is totally unsatisfactory, another instrument 42 with a different sizer head 44 is selected and the same procedure repeated.

When the selected instrument results in close to acceptable performance, the head 44 is moved back and forth in the direction of arrow 46 (FIG. 9) to determine the optimum position of the implant in the opening 14. After that location is determined and noted, the sizing head 44 is removed from the opening 14.

The physician then takes an inserter instrument 48 as shown in FIG. 11 for holding one of the implants 28A–D (see FIGS. 10A–D) which correspond with the sizing head 44 found to provide optimum performance. The instrument 48 has a notched holding end 50 with an opening 52 adapted to engage the neck 32 of the implant 28, which is formed in an "H" shape in cross-section. The notch 52 is sized to engage the H-shaped cross-section of the neck 32 with a slight friction fit so the implant can be held and inserted into the opening 44 shown in FIG. 12 and then rotated to the position shown in FIG. 7. The physician will then move the implant to the position along the length of opening 44 found to provide the best performance as determined through use of the sizer head 44.

The implant is retained in place in the opening 14 by one of the shims 36A–D (FIG. 13) selected with an opening 38 in the location which will fix the implant at the position in the opening 14 determined by the physician to provide optimum performance. As shown in FIGS. 13A–D, a series of shims 36A–D are provided with openings 38 formed to cooperate with the necks 32 on the implants 28A–D shown in FIGS. 10A–D, at various positions along the length of the opening 14.

The shims can be formed either with closed openings except for 36A as shown in FIGS. 13A–D or they can be U-shaped as shown in FIGS. 14A–D. An advantage of the shims in FIG. 13A and FIGS. 14A–D is that they can be placed in the opening 14 by the physician while the inserter instrument 48 holds the implant in place as shown in FIG. 12. If the shims of FIGS. 13B–D are used, they should be placed on the inserter instrument 48 before it engages the implant 28 and then slid down the neck 58 of the inserter into the final position shown in FIG. 7 after the implant is properly positioned.

After the shim 36 is in place, the physician can easily move a thumb control 60 on the handle of the inserter instrument 48 in the direction of arrow 62 in order to move a rod 64, which is telescopingly located inside the inserter instrument 48, to disengage the implant 28 from the notched holding end 50. After this is accomplished, the surgeon can suture the patient's skin over the opening 14 which will hold the shim and implant in place relative to the paralyzed vocal cord.

The implants 28 and shims 36 can be formed of any suitable sterilizible, biocompatible material. Preferably, they are formed of a calcium phosphate material known as hydroxylapatite which is light weight, rigid and has an outer surface compatible with adherence of tissue for permanently maintaining the implant in place. Other calcium phosphate materials such as bioglass or suitable ceramics or plastics could also be used, which are either porous to accommodate tissue ingrowth or dense. The instruments can be formed of any suitable, rigid, sterilizible material such as stainless steel.

Therefore, an implant, instruments and method are provided in accordance with the invention which allow for precise positioning of an implant for surgically repositioning a paralyzed vocal cord in minimum time. An advantage of the implant, instruments and method of the present invention is that a hard material such as hydroxylapatite can be used since the physician does not have to custom cut or carve the implant in order to provide the proper fit or to use a suitably sized piece of cartilage between the implant and the vocal cord in order to obtain proper phonation.

The foregoing description of preferred embodiments is considered to be exemplary and not limiting in any way and it is understood that the invention covers improvements and modifications which fall within the scope of the appended claims.

What is claimed is:

1. A system of phonosurgery implantation for insertion by a surgeon through an opening formed in a patient's thyroid cartilage to stabilize a vocal cord therein, the system comprising:

(a) a series of implant bodies of different sizes, the implant bodies each having a holding portion and a series of engaging means for holding the implant bodies relative to the vocal cord by engaging the holding portion of the bodies in different positions in the opening formed in the thyroid cartilage;

(b) a series of sizing instruments, each having a sizing portion corresponding respectively in size and shape to one of the implant bodies for enabling a surgeon to determine the implant body to use;

(c) inserter instrument means for engaging the selected implant body so that the surgeon can insert and move the selected implant body in the opening in the thyroid cartilage;

(d) wherein the holding portions on the implant bodies are H-shaped in cross section and substantially the same size and shape.

2. A system of phonosurgery implantation for insertion by a surgeon through an opening formed in a patient's thyroid cartilage to stabilize a vocal cord therein, the system comprising:

(a) a series of implant bodies of different sizes, the implant bodies each having a holding portion and a series of engaging means for holding the implant bodies relative to the vocal cord by engaging the holding portion of the bodies in different positions in the opening formed in the thyroid cartilage;

(b) a series of sizing instruments, each having a sizing portion corresponding respectively in size and shape to one of the implant bodies for enabling a surgeon to determine the implant body to use;

(c) inserter instrument means for engaging the selected implant body so that the surgeon can insert and move the selected implant body in the opening in the thyroid cartilage; and (d) wherein the holding portions on the implant bodies are H-shaped in cross section; and (f) the inserter instrument means includes an elongated portion with a notched-end adapted to engage the H-shaped holding portion in a releasable friction fit, the elongated portion including a telescopingly movable rod for disengaging the implant body.

3. A system of phonosurgery implantation for insertion by a surgeon through an opening formed in a patient's thyroid cartilage to stabilize a vocal cord therein, the system comprising:

(a) a series of implant bodies of different sizes, the implant bodies each having a holding portion and a series of engaging means for holding the implant bodies relative to the vocal cord by engaging the holding portion of the bodies in different positions in the opening formed in the thyroid cartilage;

(b) a series of sizing instruments, each having a sizing portion corresponding respectively in size and shape to one of the implant bodies for enabling a surgeon to determine the implant body to use;

(c) inserter instrument means for engaging the selected implant body so that the surgeon can insert and move the selected implant body in the opening in the thyroid cartilage;

(d) wherein the holding portions on the implant bodies are substantially the same size and shape; and (e) wherein the series of engaging means includes a series of shims with openings therein for engaging the holding portions of the implant bodies, the shims having openings in different locations for holding the implant bodies in different positions in the opening in the thyroid cartilage.

* * * * *